United States Patent
Satoh et al.

(10) Patent No.: US 10,377,777 B2
(45) Date of Patent: Aug. 13, 2019

(54) ANTI-FOGGING AGENT

(71) Applicant: CEKO CO., LTD., Gyeonggi-do (KR)

(72) Inventors: Masahiro Satoh, Kyoto (JP); Satsuki Kitajima, Kyoto (JP)

(73) Assignee: CEKO CO., LTD., Gyeonggi-do (KR)

( * ) Notice: Subject to any disclaimer, the term of this patent is extended or adjusted under 35 U.S.C. 154(b) by 0 days.

(21) Appl. No.: 15/767,029

(22) PCT Filed: Oct. 7, 2016

(86) PCT No.: PCT/KR2016/011266
§ 371 (c)(1),
(2) Date: Apr. 9, 2018

(87) PCT Pub. No.: WO2017/061826
PCT Pub. Date: Apr. 13, 2017

(65) Prior Publication Data
US 2018/0298039 A1    Oct. 18, 2018

(30) Foreign Application Priority Data

Oct. 9, 2015 (JP) ................. 2015-200828

(51) Int. Cl.
| | |
|---|---|
| *C07F 7/08* | (2006.01) |
| *C07F 7/18* | (2006.01) |
| *C09D 1/00* | (2006.01) |
| *C09D 5/00* | (2006.01) |
| *C09D 183/08* | (2006.01) |
| *C09D 183/12* | (2006.01) |

(52) U.S. Cl.
CPC .............. *C07F 7/1892* (2013.01); *C07F 7/08* (2013.01); *C07F 7/0878* (2013.01); *C07F 7/18* (2013.01); *C07F 7/1804* (2013.01); *C09D 1/00* (2013.01); *C09D 5/00* (2013.01); *C09D 183/08* (2013.01); *C09D 183/12* (2013.01)

(58) Field of Classification Search
None
See application file for complete search history.

(56) References Cited

U.S. PATENT DOCUMENTS

2013/0055927 A1    3/2013 Satoh et al.

FOREIGN PATENT DOCUMENTS

| CN | 1536032 A | 10/2004 |
|---|---|---|
| JP | 2001-131445 A | 5/2001 |
| JP | 2001131445 A * | 5/2001 |
| JP | 2006016578 A | 1/2006 |
| JP | 4623607 B2 | 2/2011 |
| JP | 2011153164 A | 8/2011 |
| JP | 2012-007037 A | 1/2012 |
| JP | 5750436 B2 | 7/2015 |
| KR | 10-2010-0067647 | 6/2010 |
| WO | WO-2009044912 A1 | 4/2009 |

OTHER PUBLICATIONS

Osamu, JP-2001131445-A (May 15, 2001); Machine Translation. (Year: 2001).*
International Search Report, dated Jan. 16, 2017 issued in PCT/KR2016/011266 with English Translation.

* cited by examiner

*Primary Examiner* — Clinton A Brooks
*Assistant Examiner* — Kofi Adzamli
(74) *Attorney, Agent, or Firm* — Harness, Dickey & Pierce, P.L.C.

(57) ABSTRACT

A transformed metal oxide sol, according to the present invention, has as main components: a hydrolysis product of a surface-active silane coupling agent, a transformed metal oxide sol which has been transformed by means of a hydrolysis product of a surface-active silane coupling agent, or a mixture and/or a condensate of the hydrolysis product of the surface-active silane coupling agent and the transformed metal oxide sol which has been transformed by means of the hydrolysis product of the surface-active silane coupling agent; and a mixture of transformed metal oxide sols which have been transformed by means of sulfur-containing functional groups, wherein a raw metal oxide sol of the transformed metal oxide sol is preferably an organosilica sol.

12 Claims, No Drawings

ANTI-FOGGING AGENT

CROSS-REFERENCE TO RELATED APPLICATIONS

This application is a national phase application of PCT Application No. PCT/KR2016/011266, filed on Oct. 7, 2016, which claims priority to Japanese Patent Application No. 2015-200828, Oct. 9, 2015. The entire disclosure of the applications identified in this paragraph is incorporated herein by reference.

FIELD

The present invention relates to a modified metal oxide sol having a great antifog effect which is coatable and prepared at low cost. Specifically, the present invention relates to the modified metal oxide sol which can give an antifog effect to glass, plastic or metal, etc. by being coated on them.

BACKGROUND

The present inventors already have a granted patent of a modified metal oxide sol having a sulfonic acid group (Patent document 1). Although the substrate (glass, plastic, metal, etc.) applied by a hydrophilic coating solution comprising the traditional modified metal oxide sol shows hydrophilic property, it does not show antifog effect. And when the lens treated by the coating solution is exposed to steam, water drops generate and sight becomes poor.

As the patent of the antifog additive, an antifog additive using phosphoric ester-type emulsifier (Patent document 2) and an antifog additive using polyacrylic acids (Patent document 3) have been filed.

PATENT DOCUMENTS (Patent document 1) JP 5750436 B
(Patent document 2) JP 2006-16578 A
(Patent document 3) JP 2011-153164 A

DETAILED DESCRIPTION

Technical Problem

The purpose of the present invention is to provide a modified metal oxide sol that is suitable for an antifogging additive, preventing fog when exposed to steam.

Technical Solution

In order to achieve the technical purpose, the present invention provides a modified metal oxide sol that is suitable for an antifogging additive.

The present invention comprises the below technical solutions.

[1] A modified metal oxide sol comprising a mixture and/or condensation product of a hydrolysate of a surface-active silane coupling agent, a modified metal oxide sol that is modified by a hydrolysate of a surface-active silane coupling agent or a mixture and/or a condensation product of a hydrolysate of a surface-active silane coupling agent and a modified metal oxide sol that is modified by a hydrolysate of surface-active silane coupling agent; and a modified metal oxide sol that is modified by a functional group containing sulfur (S) (hereinafter referred as "a functional group containing S-modified metal oxide sol") as the main components, wherein a surface-active silane coupling agent is a reaction product of a compound represented by the following Formula (1) and a silane coupling agent having a functional group that can react with active hydrogen of Formula (1), and the functional group containing S-modified metal oxide sol is a modified metal oxide sol in which 0.5 mmol or more of metal oxide sol based on 1 g of metal oxide sol is modified by a functional group represented by the following Formula (2):

$$R^1{-}X{-}(CH_2CH_2O)_n{-}Y \qquad (1)$$

wherein $R^1$ is $C_1$ to $C_{20}$ alkyl group (the alkyl group may comprise a benzene ring and double bond);
X is $-O-$, $-COO-$ or $-CONH-$;
n is a natural number of 1 to 30; and
Y is hydrogen or $-CH_2COOH$;

$$MOS(=O)_2{-}R^2{-}Si(CH_3)_n({-}O{-})_{3-n} \qquad (2)$$

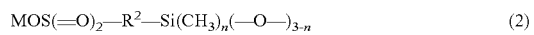

wherein M is hydrogen ion, $C_1$ to $C_4$ alkyl group, a metal ion or an ammonium group ($NR^3_4$);
$R^2$ is $C_1$ to $C_{10}$ alkylene group (the alkylene chain may comprise urethane linkage or urea linkage);
$R^3$ is the same or different $C_1$ to $C_5$ alkyl group or hydrogen; and
n is 0 or 1.

[2] The modified metal oxide sol according to [1], further comprising at least one of the silicon-based compounds represented by the following Formula (3):

$$X{-}(R^4)_m{-}Si(CH_3)_n({-}Y)_{3-n} \qquad (3)$$

wherein X is selected from the group consisting of vinyl group, thiol group, amino group, chlorine atom, acryl group, methacryl group, styryl group, phenyl group, glycydoxy group, 3,4-epoxycyclohexyl group and blocked isocyanate group;
$R^4$ is $C_1$ to $C_5$ alkylene group;
m is 0 or 1;
Y is the same or different $C_1$ to $C_4$ alkoxy group or hydroxyl group; and
n is 0 or 1.

[3] The modified metal oxide sol according to [1] or [2], wherein the metal oxide sol is organosilica sol.

[4] An antifog additive comprising the modified metal oxide sols according to any of [1] to [3].

[5] An antifog coating composition comprising the modified metal oxide sols according to any of [1] to [4].

[6] A structure that is obtained by coating and curing the antifog coating composition according to [5].

Advantageous Effects

The present invention relates to a modified metal oxide sol having a great antifog effect that is coatable and prepared at low cost.

The antifog additive of the present invention comprising the modified metal oxide sol prevents fog when exposed to steam.

Since the antifog additive comprising the modified metal oxide sol has a good antifog effect for glass or plastic, etc., it is suitable as an antifog additive for glass, lens of eyeglasses, optical lens, mirror, etc. Moreover, since the antifog additive is coatable and prepared at low cost, it is suitable for a hydrophilizing agent, an antistatic agent, a hydrophilic coating composition, an antimicrobial agent, an ion (proton) conductor as well as an antifog additive.

DISCLOSURE OF THE INVENTION

The present invention is described in detail below.

A modified metal oxide sol of the present invention comprises a mixture and/or condensation product of a hydrolysate of a surface-active silane coupling agent, a modified metal oxide sol that is modified by a hydrolysate of a surface-active silane coupling agent or a mixture and/or a condensation product of a hydrolysate of a surface-active silane coupling agent and a modified metal oxide sol that is modified by a hydrolysate of a surface-active silane coupling agent; and a modified metal oxide sol that is modified by a functional group containing sulfur (S) (hereinafter referred as "a functional group containing S-modified metal oxide sol") as the main components.

The surface-active silane coupling agent is a reaction product of a compound represented by the following Formula (1) and a silane coupling agent having a functional group that can react with active hydrogen of Formula (1).

$$R^1-X-(CH_2CH_2O)_n-Y \quad (1)$$

In the above Formula (1), $R^1$ is $C_1$ to $C_{20}$ alkyl group (the alkyl group may comprise a benzene ring and double bond); X is —O—, —COO— or —CONH—; n is a natural number of 1 to 30; and Y is hydrogen or —CH$_2$COOH.

And the functional group containing S-modified metal oxide sol is a modified metal oxide sol in which 0.5 mmol or more of metal oxide sol based on 1 g of metal oxide sol is modified by a functional group represented by the following Formula (2):

$$MOS(=O)_2-R^2-Si(CH_3)_n(-O-)_{3-n} \quad (2)$$

In the above Formula (2), M is hydrogen ion, $C_1$ to $C_4$ alkyl group, a metal ion or an ammonium group ($NR^3_4$); $R^2$ is $C_1$ to $C_{10}$ alkylene group (the alkylene chain may comprise urethane linkage or urea linkage); $R^3$ is the same or different $C_1$ to $C_5$ alkyl group or hydrogen; and n is 0 or 1.

In the compound of the above Formula (1), a raw material of the silane coupling agent, $C_1$ to $C_{20}$ alkyl group (the alkyl group may comprise a benzene ring and double bond) of $R^1$ may be methyl group, ethyl group, octyl group, decyl group, dodecyl group, tetradecyl group, pentadecyl group, hexadecyl group, palmitoleic acid group, heptadecyl group, octadecyl group, oleyl group, etc. Considering the convenience of acquiring the raw material, methyl group, dodecyl group and heptadecyl group are preferred.

The compound of Formula (1) is a surfactant, and a commercially available surfactant can be used.

X is —O—, —COO— or —CONH—.

n is a natural number of 1 to 30, and 1 to 9 are preferred considering the convenience of acquiring the raw material and handling it in liquid form.

Y is hydrogen or —CH$_2$COOH.

The compound of Formula (1) is a surfactant, and a commercially available surfactant can be used.

In the commercially available surfactant comprising the compound of Formula (1), the number of added ethylene oxides is commonly not certain. As a result, the surfactant is a mixture of the surfactants having different numbers of added ethylene oxides, not a single surfactant.

In the case of the mixture of the compounds of Formula (1), it is preferred that n be on average 9 or less considering the convenience of handling it in liquid form.

The concrete examples of the compounds of Formula (1) are as follows:

$CH_3O(CH_2CH_2O)_2H$
$CH_3O(CH_2CH_2O)_3H$
$CH_3O(CH_2CH_2O)_4H$
$CH_3O(CH_2CH_2O)_5H$
$CH_3O(CH_2CH_2O)_6H$
$C_{12}H_{25}O(CH_2CH_2O)_3CH_2COOH$
$C_{12}H_{25}O(CH_2CH_2O)_4CH_2COOH$
$C_{12}H_{25}O(CH_2CH_2O)_5CH_2COOH$
$C_{13}H_{27}O(CH_2CH_2O)_3CH_2COOH$
$C_{12}H_{25}O(CH_2CH_2O)_7H$
$C_{12}H_{25}O(CH_2CH_2O)_8H$
$C_{12}H_{25}O(CH_2CH_2O)_9H$
$C_{12}H_{25}O(CH_2CH_2O)_{10}H$
$C_{12}H_{25}O(CH_2CH_2O)_{11}H$
$C_{17}H_{35}COO(CH_2CH_2O)_9H$
$C_{17}H_{33}COO(CH_2CH_2O)_5H$
$C_{17}H_{33}COO(CH_2CH_2O)_9H$
$C_{17}H_{33}COO(CH_2CH_2O)_{14}H$
$C_{17}H_{35}CONHCH_2CH_2OH$

A silane coupling agent having a functional group that can react with active hydrogen of the compounds of Formula (1) is the silane coupling agent having any of epoxy group, isocyanate group, acid anhydride group or amino group.

Preferred silane coupling agents having a functional group that can react with active hydrogen of the compounds of Formula (1) are 3-glycydoxypropyltrimethoxysilane, 3-glycydoxypropyltriethoxysilane, 3-glycydoxypropylmethyldimethoxysilane, 3-glycydoxypropylmethyldiethoxysilane, 2-(3,4-epoxycyclohexyl)ethyltrimethoxysilane, 3-isocyanatepropyltriethoxysilane, 3-trimethoxysilylpropylsuccinic anhydride, 3-aminopropyltrimethoxysilane and 3-aminopropylmethyldimethoxysilane.

Concrete examples of the surface-active silane coupling agent, which is produced from a reaction of a compound represented by the following Formula (1) and the silane coupling agent having a functional group which can react with active hydrogen of Formula (1), are as follows:

$CH_3-O-(CH_2CH_2O)_2CH_2CH(OH)$
$CH_2OCH_2CH_2CH_2Si(OCH_3)_3$
$CH_3-O-(CH_2CH_2O)_2CH_2CH(OH)$
$CH_2OCH_2CH_2CH_2Si(CH_3)(OCH_3)_2$
$CH_3-O-(CH_2CH_2O)_3CH_2CH(OH)$
$CH_2OCH_2CH_2CH_2Si(OCH_3)_3$
$CH_3-O-(CH_2CH_2O)_3CH_2CH(OH)$
$CH_2OCH_2CH_2CH_2Si(CH_3)(OCH_3)_2$
$C_{12}H_{25}-O-(CH_2CH_2O)_6CH_2CH(OH)$
$CH_2OCH_2CH_2CH_2Si(OCH_3)_3$
$C_{12}H_{25}-O-(CH_2CH_2)_6CH_2OOOCH_2CH(OH)$
$CH_2OCH_2CH_2CH_2Si(OCH_3)_3$
$C_{12}H_{25}-O-(CH_2CH_2O)_7CH_2CH(OH)$
$CH_2OCH_2CH_2CH_2Si(OCH_3)_3$
$C_{12}H_{25}-O-(CH_2CH_2)_7CH_2OOOCH_2CH(OH)$
$CH_2OCH_2CH_2CH_2Si(OCH_3)_3$
$C_{12}H_{25}-O-(CH_2CH_2)_8CH_2COOCH_2CH(OH)$
$CH_2OCH_2CH_2CH_2Si(OCH_3)_3$
$C_{12}H_{25}-O-(CH_2CH_2)_9CH_2OOOCH_2CH(OH)$
$CH_2OCH_2CH_2CH_2Si(OCH_3)_3$
$CH_3-O-(CH_2CH_2O)_2CH_2CH_2OCONHCH_2CH_2CH_2Si(OC_2H_5)_3$
$CH_3-O-(CH_2CH_2O)_3CH_2CH_2OCONHCH_2CH_2CH_2Si(OC_2H_5)_3$
$C_{10}H_{21}-O-(CH_2CH_2O)_6CH_2CH_2OCONHCH_2CH_2CH_2Si(OC_2H_5)_3$
$C_{10}H_{21}-O-(CH_2CH_2O)_7CH_2CH_2OCONHCH_2CH_2CH_2Si(O_2H_5)_3$ $C_{10}H_{21}$—O—$(CH_2CH_2O)_8CH_2CH_2OCONHCH_2CH_2CH_2Si(O_2H_5)_3$
$C_{10}H_{21}$—O—$(CH_2CH_2O)_9CH_2CH_2OCONHCH_2CH_2CH_2Si(O_2H_5)_3$
$C_{12}H_{25}$—O—$(CH_2CH_2O)_6CH_2CH_2OCONHCH_2CH_2CH_2Si(O_2H_5)_3$
$C_{12}H_{25}$—O—$(CH_2CH_2O)_7CH_2CH_2OCONHCH_2CH_2CH_2Si(O_2H_5)_3$
$C_{12}H_{25}$—O—$(CH_2CH_2O)_8CH_2CH_2OCONHCH_2CH_2CH_2Si(O_2H_5)_3$
$C_{12}H_{25}$—O—$(CH_2CH_2O)_9CH_2CH_2OCONHCH_2CH_2CH_2Si(O_2H_5)_3$
$C_{12}H_{25}$—O—$(CH_2CH_2O)_8CH_2CONHCH_2CH_2CH_2Si(OCH_3)_3$
$C_{12}H_{25}$—O—$(CH_2CH_2O)_9CH_2CONHCH_2CH_2CH_2Si(OCH_3)_3$
$CH_3$—O—$(CH_2CH_2O)_3COCH_2CH(COOH)CH_2CH_2CH_2Si(OCH_3)_3$
$CH_3$—O—$(CH_2CH_2O)_3COCH(CH_2COOH)CH_2CH_2CH_2Si(OCH_3)_3$
$C_{12}H_{25}$—O—$(CH_2CH_2O)_7COCH_2CH(COOH)CH_2CH_2CH_2Si(OCH_3)_3$
$C_{12}H_{25}$—O—$(CH_2CH_2O)_8COCH(CH_2COOH)CH_2CH_2CH_2Si(OCH_3)_3$
$C_{17}H_{35}$—COO—$(CH_2CH_2O)_9OCH_2CH(COOH)CH_2CH_2CH_2Si(OCH_3)_3$
$C_{17}H_{33}$—COO—$(CH_2H_2CH_2O)_5COCH(CH_2COOH)CH_2CH_2CH_2CH_2Si(OCH_3)_3$

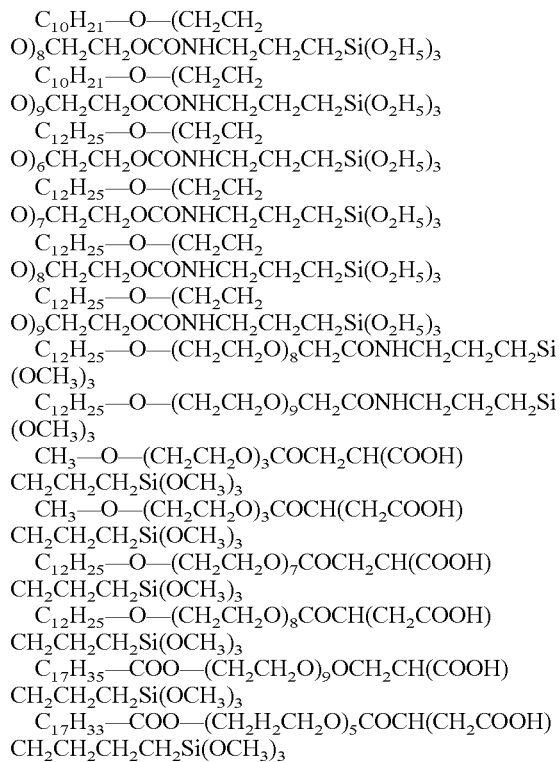

The compound of the surface-active silane coupling agent can be obtained through the following method.

The compound of the surface-active silane coupling agent is obtained by mixing the compound of the above Formula (1) and a silane coupling agent, and reacting them with each other at room temperature or during heating.

The mole ratio of the mixture of the compound of the above Formula (1) and a silane coupling agent used in the present invention may be equal, or either of them may be excessive. It is preferred that their mole ratio be equal or the ratio of the silane coupling agent is some excessive.

The reaction temperature is from room temperature to 200° C., preferably from room temperature to 100° C.

If necessary, a catalyst can be used.

When the terminal of the compound of Formula (1) is hydroxyl group and the silane coupling agent has epoxy group, acid catalyst (for example, p-toluene sulfonic acid or sulfuric acid, etc.) can be used.

And when the terminal of the surfactant is hydroxyl group and the silane coupling agent has isocyanate group, tin-based catalyst (for example, dibutyl tin diacetate and dibutyl tin dilaurate, etc.) or zirconia-based catalyst (for example, zirconium tetraacetylacetonate, etc.) can be used.

A solvent may, or may not, be used. The solvent may be ether-based solvent (tetrahydrofuran, dioxane, 1,2-dimethoxyethane, etc.), aromatic hydrocarbons (toluene, xylene, etc.), ketone-based solvent (acetone, methylethylketone, methylisobutylketone, etc.), aprotic solvent (N,N-dimethylformamide, N,N-dimethylacetamide, N-methylpyrrolidone, etc.), etc. Solvent-free is preferable.

The reaction time is usually 2 to 72 hours, preferably 8 to 48 hours.

The hydrolysate of the surface-active silane coupling agent or the modified metal oxide sol which is modified by the hydrolysate of the surface-active silane coupling agent, a raw material of the metal oxide sol of the present invention, is obtained through the following method.

The hydrolysate of the surface-active silane coupling agent can be obtained by dissolving the surface-active silane coupling agent into water-soluble solvents (for example, alcohol-based solvent [methylalcohol, ethylalcohol, isopropylalcohol, etc.], ether-based solvent [tetrahydrofuran, dioxane, etc.], ketone-based solvent [acetone, methylethylketone, etc.] or etc.), and hydrolyzing them by adding water.

By adding the metal oxide sol during hydrolysis, the modified metal oxide sol which is modified by a hydrolysate of surface-active silane coupling agent can be obtained.

The temperature during hydrolysis is not limited, and the boiling point at room temperature is preferable.

The concentration of the surface-active silane coupling agent to the solvent is 0.001 to 20 weight %, preferably 0.01 to 10 weight %.

It is not problematic if the amount of water used is equal to or more than equimolar to hydrolyzable group of the surface-active silane coupling agent.

Also, the concentration of the metal oxide sol of raw material to the solvent to be added for preparing the modified metal oxide sol which is modified by a hydrolysate of surface-active silane coupling agent is 1-50 weight %, preferably 1-30 weight %.

The amount of the silane coupling agent to the metal oxide sol is equal to or more than 0.01 mmol, preferably 0.05-10.0 mmol based on 1 g of sol.

If the amount of the silane coupling agent to the metal oxide sol is less than 0.01 mmol, the antifog effect declines because the concentration of the silane coupling agent is too low. If the amount of the silane coupling agent to the metal oxide sol is more than 10.0 mmol, self-condensation of the silane coupling agent occurs due to lack of silanol in the metal oxide and the layer-formation property declines.

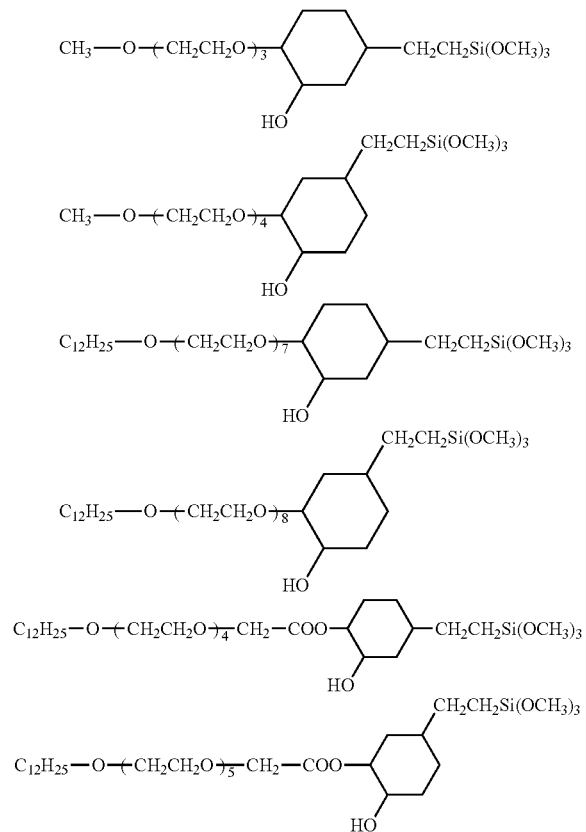

The metal oxide sol may be silica sol, alumina sol or zirconia sol, preferably silica sol, more preferably organosilica sol.

Also, the organosol is the colloidal solution which is prepared by dispersing colloidal silica with surface modification of nano level into the organic solvent such as alcohol, ketone, ether, toluene, etc.

For example, the organosol may be organosilica sol (methanol silica sol, IPA-ST, IPA-ST, IPA-ST-UP, IPA-ST-ZL, EG-ST, NPC-ST-30, DMAC-ST, MEK-ST, MIBK-ST, PMA-ST and PGM-ST) from Nissan Chemical Industries, Ltd., or high-purity organosilica sol (PL-1-IPA, PL-2L-PGME and PL-2L-MEK) from FUSO CHEMICAL CO., LTD. These may be used individually or in combination.

A functional group containing S-modified metal oxide sol will be described below.

In the above Formula (2), which is a functional group of the functional group containing S-modified metal oxide, $C_1$ to $C_{10}$ alkylene group of $R^2$ may be methylene group, ethylene group, propylene group, butylene group, pentylene group, etc. Considering cost and the convenience of acquiring the raw material, propylene group is preferred.

M of the above Formula (2) may be hydrogen ion, $C_1$ to $C_4$ alkyl group, a metal ion (alkali metal ion, alkali earth metal ion, silver ion, copper ion, nickel ion, etc.) or an ammonium ion ($NR^3_4$). Considering the antifog effect and antibacterial property, hydrogen ion, alkali metal ion, alkali earth metal ion, silver ion and ammonium ion are preferred.

The alkali metal ion or alkali earth metal ion may be lithium ion, sodium ion, potassium ion, cesium ion, magnesium ion, calcium, etc.

The alkali metal ion is preferred, and lithium ion and sodium ion are more preferred.

The concrete examples of the functional group of Formula (2) are as follows:

$HOSO_2$—$CH_2CH_2CH_2Si(—O—)_3$
$LiOSO_2$—$CH_2CH_2CH_2Si(—O—)_3$
$NaOSO_2$—$CH_2CH_2CH_2Si(—O—)_3$
$KOSO_2$—$CH_2CH_2CH_2Si(—O—)_3$
$NH_4OSO_2$—$CH_2CH_2CH_2Si(—O—)_3$
$N(CH_3)_4OSO_2$—$CH_2CH_2CH_2Si(—O—)_3$
$NH(C_2H_5)_3OSO_2$—$CH_2CH_2CH_2Si(—O—)_3$
$AgOSO_2$—$CH_2CH_2CH_2Si(—O—)_3$
$HOSO_2$—$CH_2CH_2OCONHCH_2CH_2CH_2Si(—O—)_3$
$LiOSO_2$—$CH_2CH_2OCONHCH_2CH_2CH_2Si(—O—)_3$
$NaOSO_2$—$CH_2CH_2OCONHCH_2CH_2CH_2Si(—O—)_3$
$KOSO_2$—$CH_2CH_2OCONHCH_2CH_2CH_2Si(—O—)_3$
$NH_4OSO_2$—$CH_2CH_2OCONHCH_2CH_2CH_2Si(—O—)_3$
$N(CH_3)_4OSO_2$—$CH_2CH_2OCONHCH_2CH_2CH_2Si(—O—)_3$
$NH(C_2H_5)_3OSO_2$—$CH_2CH_2OCONHCH_2CH_2CH_2Si(—O—)_3$
$AgOSO_2$—$CH_2CH_2OCONHCH_2CH_2CH_2Si(—O—)_3$
$HOSO_2$—$CH_2CH_2NHCONHCH_2CH_2CH_2Si(—O—)_3$
$LiOSO_2$—$CH_2CH_2NHCONHCH_2CH_2CH_2Si(—O—)_3$
$NaOSO_2$—$CH_2CH_2NHCONHCH_2CH_2CH_2Si(—O—)_3$
$KOSO_2$—$CH_2CH_2NHCONHCH_2CH_2CH_2Si(—O—)_3$
$NH_4OSO_2$—$CH_2CH_2NHCONHCH_2CH_2CH_2Si(—O—)_3$
$N(CH_3)_4OSO_2$—$CH_2CH_2NHCONHCH_2CH_2CH_2Si(—O—)_3$
$NH(C_2H_5)_3OSO_2$—$CH_2CH_2NHCONHCH_2CH_2CH_2Si(—O—)_3$
$AgOSO_2$—$CH_2CH_2NHCONHCH_2CH_2CH_2Si(—O—)$
$HOSO_2$—$C_6H_4NHCONHCH_2CH_2CH_2Si(—O—)_3$
$LiOSO_2$—$C_6H_4NHCONHCH_2CH_2CH_2Si(—O—)_3$
$NaOSO_2$—$C_6H_4NHCONHCH_2CH_2CH_2Si(—O—)_3$
$KOSO_2$—$C_6H_4NHCONHCH_2CH_2CH_2Si(—O—)_3$
$NH_4OSO_2$—$C_6H_4NHCONHCH_2CH_2CH_2Si(—O—)_3$
$N(CH_3)_4OSO_2$—$C_6H_4NHCONHCH_2CH_2CH_2Si(—O—)_3$
$NH(C_2H_5)_3OSO_2$—$C_6H_4NHCONHCH_2CH_2CH_2Si(—O—)_3$
$AgOSO_2$—$C_6H_4NHCONHCH_2CH_2CH_2Si(—O—)_3$
$HOSO_2$—$CH_2CH_2CH_2SiCH_3(—O—)_2$
$LiOSO_2$—$CH_2CH_2CH_2SiCH_3(—O—)_2$
$NaOSO_2$—$CH_2CH_2CH_2SiCH_3(—O—)_2$
$KOSO_2$—$CH_2CH_2CH_2SiCH3(—O—)_2$
$NH_4OSO_2$—$CH_2CH_2CH_2SiCH_3(—O—)_2$
$NH(CH_3)_3OSO_2$—$CH_2CH_2CH_2SiCH_3(—O—)_2$
$NH(C_2H_5)_3OSO_2$—$CH_2CH_2CH_2SiCH_3(—O—)_2$
$AgOSO_2$—$CH_2CH_2CH_2SiCH_3(—O—)_2$
$HOSO_2$—$CH_2CH_2OCONHCH_2CH_2CH_2SiCH_3(—O—)_2$
$LiOSO_2$—$CH_2CH_2OCONHCH_2CH_2CH_2SiCH_3(—O—)_2$
$NaOSO_2$—$CH_2CH_2OCONHCH_2CH_2CH_2SiCH_3(—O—)_2$
$KOSO_2$—$CH_2CH_2OCONHCH_2CH_2CH_2SiCH_3(—O—)_2$
$NH_4OSO_2$—$CH_2CH_2OCONHCH_2CH_2CH_2SiCH_3(—O—)_2$
$NH(CH_3)_3OSO_2$—$CH_2CH_2OCONHCH_2CH_2CH_2SiCH_3(—O—)_2$
$NH(C_2H_5)_3OSO_2$—$CH_2CH_2OCONHCH_2CH_2CH_2SiCH_3(—O—)_2$
$AgOSO_2$—$CH_2CH_2OCONHCH_2CH_2CH_2SiCH_3(—O—)_2$
$HOSO_2$—$CH_2CH_2NHCONHCH_2CH_2CH_2SiCH_3(—O—)_2$
$LiOSO_2$—$CH_2CH_2NHCONHCH_2CH_2CH_2SiCH_3(—O—)_2$
$NaOSO_2$—$CH_2CH_2NHCONHCH_2CH_2CH_2SiCH_3(—O—)_2$
$KOSO_2$—$CH_2CH_2NHCONHCH_2CH_2CH_2SiCH_3(—O—)_2$
$NH_4OSO_2$—$CH_2CH_2NHCONHCH_2CH_2CH_2SiCH_3(—O—)_2$
$NH(CH_3)_3OSO_2$—$CH_2CH_2NHCONHCH_2CH_2CH_2SiCH_3(—O—)_2$
$NH(C_2H_5)_3OSO_2$—$CH_2CH_2NHCONHCH_2CH_2CH_2SiCH_3(—O—)_2$
$AgOSO_2$—$CH_2CH_2NHCONHCH_2CH_2CH_2SiCH_3(—O—)_2$
$HOSO_2$—$C_6H_4NHCONHCH_2CH_2CH_2SiCH_3(—O—)_2$
$LiOSO_2$—$C_6H_4NHCONHCH_2CH_2CH_2SiCH_3(—O—)_2$
$NaOSO_2$—$C_6H_4NHCONHCH_2CH_2CH_2SiCH_3(—O—)_2$
$KOSO_2$—$C_6H_4NHCONHCH_2CH_2CH_2SiCH_3(—O—)_2$
$NH_4OSO_2$—$C_6H_4NHCONHCH_2CH_2CH_2SiCH_3(—O—)_2$
$NH(CH_3)_3OSO_2$—$C_6H_4NHCONHCH_2CH_2CH_2SiCH_3(—O—)_2$
$NH(C_2H_5)_3OSO_2$—$C_6H_4NHCONHCH_2CH_2CH_2SiCH_3(—O—)_2$
$AgOSO_2$—$C_6H_4NHCONHCH_2CH_2CH_2SiCH_3(—O—)_2$

The metal oxide sol which is a raw material of the functional group containing S-modified metal oxide may be silica sol, alumina sol or zirconia sol, which is the same metal oxide sol added for preparing the modified metal oxide sol which is modified by a hydrolysate of the surface-active silane coupling agent. Silica sol is preferable, and organosilica sol is more preferable.

Also, the organosol is the colloidal solution which is prepared by dispersing colloidal silica with surface modification of nano level into the organic solvent such as alcohol, ketone, ether, toluene, etc.

For example, the organosol may be organosilica sol (methanol silica sol, IPA-ST, IPA-ST, IPA-ST-UP, IPA-ST-ZL, EG-ST, NPC-ST-30, DMAC-ST, MEK-ST, MIBK-ST, PMA-ST and PGM-ST) from Nissan Chemical Industries, Ltd., or high-purity organosilica sol (PL-1-IPA, PL-2L-PGME and PL-2L-MEK) from FUSO CHEMICAL CO., LTD. These may be used individually or in combination.

The functional group containing S-modified metal oxide sol, a raw material of the metal oxide sol of the present invention, is obtained through the following method.

The functional group containing S-modified metal oxide sol is obtained by adding silane coupling agents of the below Formulas (SC1) or (SC2) having a functional group which can be converted to sulfonic acid group chemically into metal oxide sol, reacting silanol of metal oxide sol with silane coupling agents and converting thiol group to sulfonic acid group, and if necessary, neutralizing them with a base.

$$HS-R^1-Si(CH_3)_n(-Y)_{3-n} \quad (SC1)$$

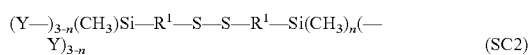

$$(Y-)_{3-n}(CH_3)Si-R^1-S-S-R^1-Si(CH_3)_n(-Y)_{3-n} \quad (SC2)$$

In the above Formulas, $R^1$ is $C_1$ to $C_{10}$ alkylene group (the alkylene chain may comprise urethane linkage or urea linkage); Y is the same or different $C_1$ to $C_4$ alkoxy group or hydroxyl group, and n is 0 or 1.

The concrete examples of the silane coupling agents of the below Formulas (SC1) or (SC2) are as follows:

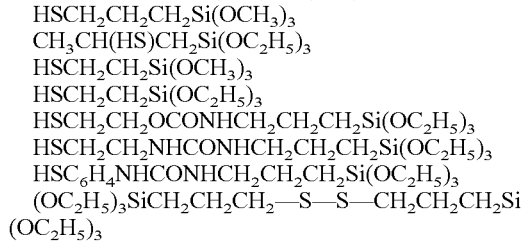

HSCH$_2$CH$_2$CH$_2$Si(OCH$_3$)$_3$
CH$_3$CH(HS)CH$_2$Si(OC$_2$H$_5$)$_3$
HSCH$_2$CH$_2$Si(OCH$_3$)$_3$
HSCH$_2$CH$_2$Si(OC$_2$H$_5$)$_3$
HSCH$_2$CH$_2$OCONHCH$_2$CH$_2$CH$_2$Si(OC$_2$H$_5$)$_3$
HSCH$_2$CH$_2$NHCONHCH$_2$CH$_2$CH$_2$Si(OC$_2$H$_5$)$_3$
HSC$_6$H$_4$NHCONHCH$_2$CH$_2$CH$_2$Si(OC$_2$H$_5$)$_3$
(OC$_2$H$_5$)$_3$SiCH$_2$CH$_2$CH$_2$—S—S—CH$_2$CH$_2$CH$_2$Si(OC$_2$H$_5$)$_3$

Among these, the compound comprising urethane linkage or urea linkage can be obtained by reacting a silane coupling agent having isocyanate group with 2-mercapto ethanol, 2-mercapto ethyl amine or 4-mercapto aniline.

In the case of reacting the metal oxide sol with the silane coupling agents of the below Formulas (SC1) or (SC2), the solvent may be alcohol-based solvent (methanol, ethanol, isopropanol, n-butanol, t-butanol, pentanol, ethyleneglycol, propyleneglycol and 1,4-butanediol, etc.), ether-based solvent (diethyl ether, tetrahydrofuran, dioxane, etc.), ketone-based solvent (acetone, methylethylketone, etc.), aprotic solvent (dimethyl sulfoxide, N,N-dimethylformamide, etc.) or the mixture thereof.

The alcohol-based solvent is preferable and one or more alcohol-based solvents can be used.

The concentration of the metal oxide sol—raw material—to the solvent is 1 to 50 weight %, preferably 1 to 30 weight %.

The amount of the silane coupling agents having a functional group which can be converted to sulfonic acid group chemically is equal to or more than 0.5 mmol, preferably 0.5 to 10.0 mmol based on 1 g of metal oxide sol.

If the amount is less than 0.5 mmol, the hydrophilic property declines due to too-low concentration of sulfonic acid group which is converted chemically. If the amount is more than 10.0 mmol, self-condensation of the silane coupling agent having a functional group which can be converted to sulfonic acid group chemically may occur due to lack of silanol in the metal oxide and the layer-formation property declines.

The temperature at the time of adding the silane coupling agents having a functional group which can be converted to sulfonic acid group chemically is not limited, and the boiling point at room temperature is preferable.

The reaction temperature is not limited, and the boiling point at room temperature is preferable.

The reaction time is not limited, but is preferably 10 minutes to 48 hours, more preferably 6 to 24 hours.

After the step of bonding the silane coupling agents having a functional group which can be converted to sulfonic acid group chemically to the metal oxide sol, the functional group may be converted to sulfonic acid group chemically by adding peroxide.

The peroxide may be organic peroxide (peracetic acid, m-chloroperbenzoic acid, benzoyl peroxide, etc.) and inorganic peroxide (ozone, hydrogen peroxide, calcium peroxide, etc.). Hydrogen peroxide and peracetic acid are preferable, and hydrogen peroxide is more preferable.

The peroxide may be added at one time or in parts during the previous step (the step of bonding the silane coupling agents having a functional group which can be converted to sulfonic acid group chemically to the metal oxide sol).

The amount of peroxide used may be 200 to 5,000 mol %, preferably 300 to 5,000 mol %, more preferably 500 to 5,000 mol % based on the silane coupling agents having a functional group which can be converted to sulfonic acid group.

The temperature at which the peroxide is added is not limited, and room temperature (about 20° C.) is preferable.

The reaction temperature is not limited, and the boiling point at room temperature (about 20° C.) is preferable.

The reaction time is not limited, preferably 10 minutes to 48 hours, more preferably 6 to 24 hours.

After converting the functional group to sulfonic acid group, the reaction solution may be neutralized with a base as needed.

The base may be hydroxides (lithium hydroxide, sodium hydroxide, potassium hydroxide, cesium hydroxide, magnesium hydroxide, calcium hydroxide, etc.), acetates (lithium acetate, sodium acetate, potassium acetate, silver acetate, etc.), metal oxide (silver oxide, etc.), ammonia, trimethylamine, triethylamine, tetramethylammonium hydroxide, tetraethylammonium hydroxide, etc.

The temperature at neutralization is not limited, and the room temperature is preferable.

The base may be added as it is, or after being diluted with the solvent (for example, water, etc.).

The method for preparing the modified metal oxide sol of the present invention will be described in detail below.

The modified metal oxide sol of the present invention can be obtained by mixing a hydrolysate of the surface-active silane coupling agent, a modified metal oxide sol which is modified by a hydrolysate of the surface-active silane coupling agent or a mixture and/or condensation product of a hydrolysate of the surface-active silane coupling agent and a modified metal oxide sol which is modified by a hydrolysate of surface-active silane coupling agent (hereinafter referred as "a hydrolysate of the surface-active silane coupling agent group") with a functional group containing S-modified metal oxide sol in solution form.

The solvent may be ether-based solvent (tetrahydrofuran, dioxane, 1,2-dimethoxyethane, etc.), aromatic hydrocarbons (toluene, xylene, etc.), ketone-based solvent (acetone, methylethylketone, methylisobutylketone, etc.), aprotic solvent (N,N-dimethylformamide, N,N-dimethylacetamide, N-methylpyrrolidone, etc.), etc.

The mixing order is not limited.

The hydrolysate of the surface-active silane coupling agent group may be added into the functional group containing S-modified metal oxide sol, or the otherwise may be good.

Also, the hydrolysate of surface-active silane coupling agent group and the functional group containing S-modified metal oxide sol may be added at one time, or either of the two may be added in parts—for example, by instillation.

The temperature during mixing is not limited within the reflux temperature of the solution used.

Heating under reflux after mixing is preferable.

The reflux time is 1 to 48 hours, preferably 4 to 24 hours.

The mixing ratio of the hydrolysate of the surface-active silane coupling agent group and the functional group containing S-modified metal oxide sol is 1 to 1,000 weight %, preferably 10 to 100 weight % of solid of the hydrolysate of the surface-active silane coupling agent group based on solid of the functional group containing S-modified metal oxide sol.

The modified metal oxide sol may further comprise at least one of the silicon-based compounds represented by the following Formula (3):

$$X—(R^4)_m—Si(CH_3)_n(—Y)_{3-n} \quad (3)$$

wherein X is selected from the group consisting of $C_1$ to $C_{20}$ linear or branched alkyl group, vinyl group, thiol group, amino group, chlorine atom, acryl group, methacryl group, alkyl ester group, styryl group, phenyl group, imidazolyl group, glycydoxy group, 3,4-epoxycyclohexyl group and blocked isocyanate group, $R^4$ is $C_1$ to $C_5$ alkylene group, m is 0 or 1, Y is the same or different $C_1$ to $C_4$ alkoxy group or hydroxyl group, and n is 0 or 1.

The modified metal oxide sol comprising the silicon-based compounds of Formula (3) can be obtained by the following method.

The condensation reaction generally occurs between the silicon-based compounds and silanol of the metal oxide sol.

The modified metal oxide sol comprising the silicon-based compounds of Formula (3) can be obtained by adding the silicon-based compounds of Formula (3) into a solution of the functional group containing S-modified metal oxide sol or into a solution of the modified metal oxide sol comprising the hydrolysate of the surface-active silane coupling agent group and the functional group containing S-modified metal oxide sol, and condensation-reacting them with the hydroxyl group (for example, silanol) of the metal oxide sol.

The silicon-based compounds of Formula (3) are as follows:

$CH_3Si(OCH_3)_3$
$CH_3Si(OC_2H_5)_3$
$C_8H_{17}Si(OCH_3)_3$
$C_8H_{17}Si(OC_2H_5)_3$
$C_{18}H_{37}Si(OCH_3)_3$
$C_{18}H_{37}Si(O_2H_5)_3$
$CH_2=CHSi(OCH_3)_3$
$CH_2=CHSi(OC_2H_5)_3$
$H_2NCH_2CH_2CH_2Si(OCH_3)_3$
$H_2NCH_2CH_2CH_2Si(OC_2H_5)_3$
$ClCH_2CH_2CH_2Si(OCH_3)_3$
$SHCH_2CH_2CH_2Si(OCH_3)_3$
$SHCH_2CH_2CH_2Si(CH_3)(OCH_3)_2$
$CH_2=CHCOOCH_2CH_2CH_2Si(OCH_3)_3$
$CH_2=C(CH_3)COOCH_2CH_2CH_2Si(OCH_3)_3$
$C_6H_5Si(OCH_3)_3$
$C_6H_5Si(OC_2H_5)_3$
$(CH_3)_3COCOCH_2CH_2SCH_2CH_2CH_2Si(OCH_3)_3$
$(CH_3)_3COCOCH_2CH_2SCH_2CH_2CH_2(CH_3)Si(OCH_3)_2$

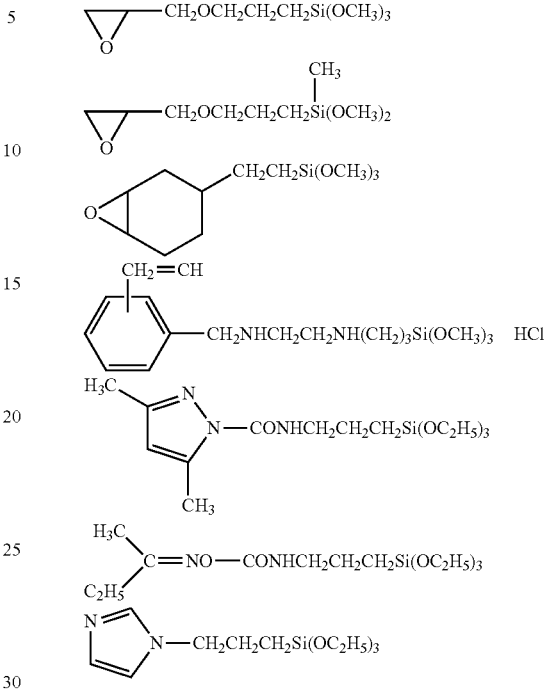

The amount of added silicon-based compounds of Formula (3) is generally 0.01-5.0 mmol, preferably 0.01-3.0 mmol based on 1 g of the total of a modified metal oxide sol that is modified by a hydrolysate of the surface-active silane coupling agent, a functional group containing S-modified metal oxide sol and metal oxide sol which is used in the synthesis of a hydrolysate of the surface-active silane coupling agent and a functional group containing S-modified metal oxide sol (hereinafter referred as "raw material metal oxide sol").

In the above range, the properties of the silicon-based compounds (for example, dispersibility, adhesion to the substrate, curing property, etc.) can be enhanced, self-condensation of the silicon-based compounds of Formula (3) does not occur, and the layer-formation property is improved.

The temperature at the time of adding the silicon-based compounds of Formula (3) is not limited, and the boiling point at room temperature is preferable.

The reaction temperature is not limited, and the boiling point is preferably at room temperature.

The reaction time is not limited, but is preferably 2 to 48 hours, more preferably 8 to 24 hours.

In the case that the silicon-based compounds of Formula (3) is stable for oxidation, a functional group of the silane coupling agent can be converted to sulfonic acid group chemically by reacting with peroxide, after reacting a silane coupling agent having a functional group which can be converted to sulfonic acid group chemically and the silicon-based compounds of Formula (3) with the metal oxide sol at the same time.

The modified metal oxide sol of the present invention may further comprise metal alkoxide, metallic chelate and/or oligomer thereof.

The metal alkoxide or metallic chelate can be represented by the following Formulas (4) and (5).

$$M(OR^5)_4 \tag{4}$$

$$M(OR^5)_2R^6_2 \tag{5}$$

wherein M is silicon, titanium or zirconium, $R^5$ is alkyl group, preferably $C_1$ to $C_8$ lower alkyl group, more preferably $C_1$ to $C_4$ lower alkyl group.

$R^5$ may be methyl group, ethyl group, propyl group, isopropyl group, butyl group, pentyl group, hexyl group, etc.

$R^6$ may be β-diketone group, specifically β-acetylacetonate group, etc.

The condensation reaction generally occurs between the metal alkoxide, metallic chelate and/or oligomer thereof and the hydroxyl group (for example, silanol) of the metal oxide sol.

The solution of the modified metal oxide sol of the present invention can be obtained by adding metal alkoxide, metallic chelate and/or oligomer thereof into a solution of the functional group containing S-modified metal oxide sol or into a solution of the modified metal oxide sol comprising the hydrolysate of the surface-active silane coupling agent group and the functional group containing S-modified metal oxide sol, and condensation-reacting them with silanol of the metal oxide sol.

The metal alkoxide oligomer may be methylsilicate, ethylsilicate or etc. from COLCOAT CO., Ltd., ATORON (NSi-500), etc. from NIPPON SODA CO., LTD., or ORGATIX TC-130, ORGATIX PC-200, ORGATIX PC-250, ORGATIX PC-601, ORGATIX PC-620, etc. from Matsumoto Fine Chemical Co., Ltd.

The amount of added metal alkoxide, metallic chelate and/or oligomer thereof is generally 0.1 to 500 weight %, preferably 0.5 to 200 weight %, more preferably 1.0 to 100 weight % based on the raw material metal oxide sol.

In the above range, the properties of the metal alkoxide, metallic chelate and/or oligomer thereof (for example, dispersibility, curing property, etc.) can be enhanced, and the layer-formation property and durability are improved.

The temperature at the time of adding metal alkoxide, metallic chelate and/or oligomer thereof is not limited, and the boiling point is preferably at room temperature.

The reaction temperature is not limited, and the boiling point is preferably at room temperature.

The reaction time is not limited, preferably 2 to 48 hours, more preferably 8 to 24 hours.

The metallic salts or bases may be added into the modified metal oxide sol of the present invention to accelerate curing.

The metallic salts may be hydroxide (lithium hydroxide, sodium hydroxide, potassium hydroxide, cesium hydroxide, magnesium hydroxide, calcium hydroxide, etc.), acetate (lithium acetate, sodium acetate, potassium acetate, silver acetate, etc.), nitrate (calcium nitrate, barium nitrate, etc.) and metal oxide (silver oxide, etc.).

The bases may be ammonia, trimethylamine, triethylamine, tetramethylammonium hydroxide, tetraethyl ammonium hydroxide, etc.

The amount of added metallic salts or bases is generally 0.01 to 500 weight %, preferably 0.05 to 200 weight %, more preferably 0.1 to 100 weight % based on the modified metal oxide sol.

The modified metal oxide sol of the present invention may also comprise a compound having plural hydroxyl groups, amino groups, epoxy groups, carboxyl groups, thiol groups, blocked isocyanate groups, etc.

The compound may be polyethyleneglycol, polytetramethyleneglycol, polyester-based diol, polycarbonate-based diol, polycaprolactone-based diol, bisphenol A-epichlorohydrin resin, epoxy novolac resin, alicyclic epoxy resin, brominated epoxy resin, aliphatic epoxy resin, polyfunctional epoxy resin, polyethyleneimine, pentaerythritoltetrakis (3-mercaptobutyrate), 1,12-dodecanedioic acid, ε-caprolactam, methylethylketoxime, 3,5-dimethylpyrazole-blocked isophorone diisocyanate, 4,4'-dicyclohexylmethanediisocyanate, hexamethylenediisocyanate, toluenediisocyanate, etc.

By putting the modified metal oxide sol of the present invention into the solvent, it may be used as an antifog additive.

The solvent—which does not react with the modified metal oxide sol and dissolve and/or disperse it—is not limited. For example, the solvent may be ether-based solvent (tetrahydrofuran, dioxane, etc.), alcohol-based solvent (methylalcohol, ethylalcohol, n-propylalcohol, iso-propylalcohol, n-butylalcohol, etc.), ketone-based solvent (acetone, methylethylketone, methylisobutylketone, etc.) and aprotic solvent (N,N-dimethylformamide, N,N-dimethylacetamide, N-methylpyrrolidone, dimethyl sulfoxide, etc.) and water.

By putting the modified metal oxide sol of the present invention into the coating solution, it may be used as an antifog coating composition.

The coating solution may be a hard coating agent, an anti-reflective coating agent, an infrared absorption coating agent, a gas barrier coating agent, an anti-static coating agent, an ultraviolet ray absorption coating agent, etc.

The antifog coating composition of the present invention may further comprise a dilution solvent to enhance workability (handling and coatability). The dilution solvent—which does not react with the modified metal oxide sol and dissolve and/or disperse it—is not limited. For example, the dilution solvent may be ether-based solvent (tetrahydrofuran, dioxane, etc.), alcohol-based solvent (methylalcohol, ethylalcohol, n-propylalcohol, iso-propylalcohol, n-butylalcohol, etc.), ketone-based solvent (acetone, methylethylketone, methylisobutylketone, etc.) and aprotic solvent (N,N-dimethylformamide, N,N-dimethylacetamide, N-methylpyrrolidone, dimethyl sulfoxide, etc.) and water.

In the case that the antifog coating composition comprises the dilution solvent, the amount of the dilution solvent is chosen so as to make the content of the modified metal oxide sol 0.01 to 15 weight % (preferably 0.05 to 10 weight %, more preferably 0.1 to 7.5 weight %) based on total solvent.

The antifog coating composition of the present invention may further comprise a surfactant to enhance workability (wettability to the substrate). The surfactant may be common hydrocarbon-based surfactant or a fluoro-based surfactant (anionic surfactant, cationic surfactant, nonionic surfactant, amphoteric surfactant). The fluoro-based surfactant which shows effectiveness with a small amount is preferable.

The concrete examples of fluoro-based surfactant may be FTERGENT (brand name) from Neos Corporation as follows.

FTERGENT 100, FTERGENT 100C, FTERGENT 110, FTERGENT 150, FTERGENT 150CH, FTERGENT A-K, FTERGENT 501, FTERGENT 250, FTERGENT 251, FTERGENT 222F, FTERGENT 208G, FTERGENT 300, FTERGENT 310 and FTERGENT 400SW.

The antifog coating composition of the present invention can be applied on a substrate, sheet, film and fiber such as glass, plastic (polymethylmethacrylate, polyethyleneterephthalate, polybutyleneterephthalate, polyethylenenaphthalate, ABS, polycarbonate, polystyrene, epoxy, unsaturated polyester, melamine, diallylphthalate, polyimide, urethane, nylon, polyethylene, polypropylene, polyvinyl chloride, polybutadiene, polyisoprene, SBR, nitrile rubber, EPM, EPDM, epichlorohydrin rubber, neoprene rubber, polysulfide, butyl rubber, etc.), metal (iron, aluminium, stainless steel, titanium, copper, brass and alloy thereof, etc.), cellulose, cellulose derivatives, cellulose analogs (chitin, chitosan and porphyrin, etc.) or natural fiber (silk, cotton, etc.) for surface antifogging.

If necessary, the surface activation treatment (the treatment for elevating surface energy) such as primer treatment, plasma treatment, ultraviolet treatment or corona discharge treatment may be conducted to enhance the adhesive property to the substrate.

The method of applying the coating solution comprising the antifog coating composition of the present invention may be dip coating, spin coating, flow coating, spray coating, etc.

After applying the coating solution by the above method and drying it, the mechanical property and chemical property of the coating layer can be enhanced by treating the material enhancing dehydrating condensation (for example, basic material: ammonia gas, etc.) for curing the formed coating layer.

Or, the mechanical property and chemical property of the coating layer can be enhanced by conducting dehydrating condensation through heat treatment and curing.

Or, both of the two methods can be employed.

If the silicon-based compounds of Formula (3) are polymerizable by some means other than radical polymerization, cationic polymerization and dehydrating condensation such as ene-thiol reaction, polymerization by light or heat and dehydrating condensation can be conducted. Polymerization and dehydrating condensation can be conducted at the same time. The light may be ultraviolet ray, visible ray, etc.

The compound which generates base or acid by light or heat can be used.

If the silicon-based compounds of Formula (3) are polymerizable, initiators that generate radicals by light or heat can be used.

Photoinitiators may be photoradical initiators such as 1-hydroxy-cyclohexyl-phenyl-ketone (IRGACURE 184), 2-benzyl-2-dimethylamino-1-(4-morpholino phenyl)-butanone-1 (IRGACURE 369), eutectic mixture of 1-hydroxy-cyclohexyl-phenyl-ketone (IRGACURE 184) and benzophenone (IRGACURE 500) 2,2-dimethoxy-1,2-diphenylethane-1-one (IRGACURE 651), bis($\eta^5$-2,4-cyclopentadiene-1-yl)-bis (2,6-difluoro-3-(1H-pyrrol-1-yl)-phenyl)titanium (IRGACURE 784), bis(2,4,6-trimethylbenzoyl)-phenylphosphine oxide (IRGACURE 819), 2-methyl-1[4-(methylthio)phenyl]-2-[morpholinopropan]-1-one (IRGACURE 907), 2-hydroxy-2-methyl-1-phenyl-propan-1-one (DAROCUR 1173), 1-[4-(2-hydroxyethoxy)-phenyl]-2-hydroxy-2-methyl-1-propan-1-one (IRGACURE 2959), liquid mixture having a ratio of 1-hydroxy-cyclohexyl-phenyl-ketone (IRGACURE 184) to 2-hydroxy-2-methyl-1-phenyl-propan-1-one (DAROCUR 1173) is 1:4 (IRGACURE 1000), mixture having a ratio of bis(2,6-dimethoxybenzoyl)-2,4,4-trimethyl-pentylphosphine oxide to 2-hydroxy-2-methyl-1-phenyl-propan-1-one (DAROCUR 1173) is 1:3 (IRGACURE 1700), mixture having a ratio of bis(2,6-dimethoxybenzoyl)-2,4,4-trimethyl-pentylphosphine oxide to 1-hydroxy-cyclohexyl-phenyl-ketone (IRGACURE 184) is 1:3 (IRGACURE 1800) and mixture having a ratio of bis(2,6-dimethoxybenzoyl)-2,4,4-trimethyl-pentylphosphine oxide to 1-hydroxy-cyclohexyl-phenyl-ketone (IRGACURE 184) is 1:1 (IRGACURE 1850), etc., cationic photoinitiators such as bis(4-tert-butylphenyl)iodonium hexafluorophosphate, bis(4-tert-butylphenyl)iodonium trifluoromethane sulfonate, diphenyliodonium hexafluoroalginate, diphenyliodonium hexafluorophosphate, diphenyliodonium trifluoromethanesulfonate, 4-isopropyl-4'-methyl diphenyliodonium tetrakis(pentafluorophenyl)borate, triphenyl sulfonium tetrafluoroborate, tri-p-tolylsulfonium hexafluorophosphate and tri-p-tolylsulfonium trifluoromethanesulfonate.

The thermal initiator may be an azo-based initiator such as $\alpha,\alpha'$-azobisisobutyronitrile, 2,2'-azobis(4-methoxy-2,4-dimethylvaleronitrile), 2,2'-azobis(2,4-dimethylvaleronitrile), dimethyl 2,2'-azobis(2-methylpropionate), 2,2'-azobis (methylbutyronitrile, 1,1'-azobis(cyclohexane-1-carbonitrile), 2,2-azobis[N-(2-prophenyl)-2-methyl propionamide], 1-[(1-cyano-1-methylethyl)azo]formamide, 2,2'-azobis(N-butyl-2-methylpropionamide) and 2,2'-azobis (N-cyclohexyl-2-methylpropionamide, etc., peroxide-based initiator such as tert-butylperoxy-2-ethylhexanoate, tert-hexylperoxy-2-ethylhexanoate, 1,1,3,3-tetramethylbutylperoxy-2-ethylhexanoate, 2,5-dimethyl-2,5-di(2-ethylhexanoylperoxy)hexane, tert-butylperoxypivalate, tert-hexylperoxypivalate, tert-butylperoxyneodecanoate, benzoylperoxide, dilauroylperoxide, di(3,5,5-trimethylhexanoyl)peroxide, tert-butylhydroperoxide, 1,1,3,3-tetramethylbutylhydroperoxide, tert-butylcumylperoxide, di-tert-hexylperoxide, diisopropylperoxydicarbonate, di-2-ethylhexylperoxydicarbonate, etc.

The catalyst thereof can be coated after adding it to the coating solution, or by spraying the solution dissolving the catalyst after layer formation or by exposure to a catalytic atmosphere.

In the case of curing by only heat treatment, the temperature of the heat treatment is generally 60-250° C., preferably 80-225° C., more preferably 80-200° C.

The heat treatment time is generally 0.05-48 hours, preferably 0.1-48 hours, more preferably 0.5-36 hours.

In the case of using dehydrating condensation catalyst, the temperature of the heat treatment is from room temperature to the above temperature, and the heat treatment time is the same as given above.

In the case of using a photoinitiator, the intensity of the irradiated light is generally 100-3,000 mJ, preferably 500-2,000 mJ, more preferably 750-2,000 mJ.

In the case of using a thermal initiator, the temperature of the heat treatment is generally 60-250° C., preferably 80-225° C., more preferably 80-200° C.

DISCLOSURE OF THE INVENTION

The present invention will be described in more detail through the Examples. However, these Examples are only intended to describe the present invention exemplarily, and the protected circumstances of the present invention are not at all limited by them.

Comparative Example 1

(1) After dissolving 15.0 g (76.5 mmol) of 3-(trimethoxysilyl)propane-1-thiol into 375 g of ethanol, 90.0 g of organosilica sol (30% isopropanol solution, IPA-ST from NISSAN CHEMICAL INDUSTRIES, LTD.) and 100.0 g of water were added to them, and heating under reflux was conducted for 24 hours. After cooling the mixture, 52.5 g (463 mmol) of hydrogen peroxide water was added to it, and heating under reflux was conducted during 24 hours. After termination of reaction, the mixture was cooled to room temperature, and 3.21 g (76.5 mmol) of lithium hydroxide monohydrate dissolved in 15 g of water was added to it for neutralization. In addition, by adding water to the mixture to make its weight 750 g, 750.0 g of ethanol solution comprising LiOSO$_2$—CH$_2$CH$_2$CH$_2$Si group-modified silica sol (2.83 mmol of lithium sulfonate is bonded based on 1 g of silica sol) was obtained.

Example 1

(1) By reacting 7.57 g of surfactant (BEAULIGHT LCA-H, polyoxyethylene lauryl ether acetate, acid value: 107) from Sanyo Chemical Industries, Ltd. with 3.4 g of 3-glycidoxypropyltrimethoxysilane for 2 days at 100° C. under Ar atmosphere, 10.3 g of surface-active silane coupling agent in which BEAULIGHT LCA-H and 3-glycidoxypropyl trimethoxysilane were bonded to each other through ester linkage was obtained. Through $^1$H-NMR detection, it was confirmed that the absorption of proton (2.62, 2.80, 3.16 ppm) at epoxy ring of 3-glycidoxypropyltrimethoxysilane—raw material—disappeared.

(2) By dissolving 1.0 g of the surface-active silane coupling agent from (1) into 48 g of ethanol, adding 1 g of water to the mixture and heating under reflux overnight, 50.0 g of ethanol solution comprising a hydrolyzed product of the surface-active silane coupling agent was obtained.

(3) By dissolving 2.5 g of ethanol solution from Comparative Example (1) and 1.0 g of ethanol solution from (2) into 46.5 g of ethanol, 50.0 g of ethanol solution comprising the antifog additive of the present invention was obtained.

Example 2

(1) By reacting 10.0 g of surfactant (EMULMIN L-90-S, ethylene oxide adduct of dodecyl alcohol, hydroxyl value: 98.3) from Sanyo Chemical Industries, Ltd. with 4.33 g (17.5 mmol) of 3-isocyanatepropyltriethoxysilane for 2 days at 100° C. under Ar atmosphere, 13.8 g of the surface-active silane coupling agent in which 3-isocyanatepropyltriethoxysilane and EMULMIN L-90-S were bonded to each other through urethane linkage was obtained. Through $^1$H-NMR detection, it was confirmed that the absorption of proton (3.27-3.32 ppm) of carbon which is bonded to isocyanate group of 3-(triethoxysilyl)propylisocyanate-raw material-disappeared and the absorption of proton (3.15-3.17 ppm) of carbon which is bonded to carbamate group of the object newly appeared.

(2) By dissolving 1.0 g of the surface-active silane coupling agent from (1) into 48.0 g of ethanol, adding 1.0 g of water to the mixture and heating under reflux overnight, 50.0 g of ethanol solution comprising hydrolyzed product of surface-active silane coupling agent was obtained.

(3) By dissolving 2.5 g of ethanol solution from Comparative Example (1) and 1.0 g of ethanol solution from (2) into 46.5 g of ethanol, 50.0 g of ethanol solution comprising the antifog additive of the present invention was obtained.

Example 3

(1) By reacting 20.2 g of surfactant (EMULMIN L-90-S, ethylene oxide adduct of dodecyl alcohol, hydroxyl value: 98.3) from Sanyo Chemical Industries, Ltd. with 8.4 g of 3-glycidoxypropyltrimethoxysilane using 0.1 g of p-toluene sulfonic acid as a catalyst for 2 days at 100° C. under Ar atmosphere, 28.1 g of surface-active silane coupling agent in which EMULMIN L-90-S and glycidoxypropyl trimethoxysilane were bonded to each other through ether linkage was obtained. Through 1H-NMR detection, it was confirmed that the absorption of proton (2.62, 2.80, 3.16 ppm) at epoxy ring of 3-glycidoxypropyltrimethoxysilane-raw material-disappeared.

(2) By dissolving 1.0 g of the surface-active silane coupling agent from (1) into 48.0 g of ethanol, adding 1 g of water to the mixture and heating under reflux overnight, 50.0 g of ethanol solution comprising hydrolyzed product of surface-active silane coupling agent was obtained.

(3) By dissolving 2.5 g of ethanol solution from Comparative Example (1) and 1.0 g of ethanol solution from (2) into 46.5 g of ethanol, 50.0 g of ethanol solution comprising the antifog additive of the present invention was obtained.

Example 4

(1) After dissolving 4.0 g of the surface-active silane coupling agent from (1) of Example 3 into 33.5 g of ethanol, 6.0 g of organosilica sol (30% isopropanol solution, IPA-ST from NISSAN CHEMICAL INDUSTRIES, LTD.) and 6.5 g of water were added to them, and heating under reflux was conducted for 24 hours to obtain 50.0 g of ethanol solution comprising ethylene oxide adduct group of dodecyl alcohol-modified silica sol (about 2.78 mmol of ethylene oxide adduct group of dodecyl alcohol is bonded based on 1 g of silica sol).

(2) By dissolving 1.25 g of ethanol solution from Comparative Example (1) and 1.25 g of ethanol solution from (1) into 47.5 g of ethanol, and heating under reflux overnight, 50.0 g of ethanol solution comprising the antifog additive of the present invention was obtained.

Example 5

(1) By reacting 16.4 g (100.0 mmol) of triethyleneglycol monomethylether (Tokyo Chemical Industry Co., Ltd.) with 24.7 g (100.0 mmol) of 3-isocyanatepropyltriethoxysilane for 2 days at 100° C. under Ar atmosphere, 40.5 g of the surface-active silane coupling agent in which 3-isocyanatepropyltriethoxysilane and triethyleneglycol monomethylether were bonded to each other through urethane linkage was obtained. Through 1H-NMR detection, it was confirmed that the absorption of proton (3.27-3.32 ppm) of carbon which is bonded to isocyanate group of 3-(triethoxysilyl)propylisocyanate—raw material—disappeared and the absorption of proton (3.13-3.18 ppm) of carbon which is bonded to carbamate group of the object newly appeared.

(2) By dissolving 1.0 g of the surface-active silane coupling agent from (1) into 48.0 g of ethanol, adding 1 g of water to the mixture and heating under reflux overnight, 50.0 g of ethanol solution comprising hydrolyzed product of the surface-active silane coupling agent was obtained.

(3) By dissolving 2.5 g of ethanol solution from Comparative Example (1) and 1.0 g of ethanol solution from (2) into 46.5 g of ethanol, 50.0 g of ethanol solution comprising the antifog additive of the present invention was obtained.

Example 6

(1) After dissolving 2.1 g of the surface-active silane coupling agent from (1) of Example 5 into 35.4 g of ethanol, 6.0 g of organosilica sol (30% isopropanol solution, IPA-ST from NISSAN CHEMICAL INDUSTRIES, LTD.) and 6.5 g of water were added into them, and heating under reflux was conducted for 24 hours to obtain 50.0 g of ethanol solution comprising triethyleneglycol monomethylether group-modified silica sol (about 2.83 mmol of triethyleneglycol monomethylether group is bonded based on 1 g of silica sol).

(2) By dissolving 1.0 g of ethanol solution from (1) and 2.5 g of ethanol solution comprising LiOSO$_2$—CH$_2$CH$_2$CH$_2$Si(—O—)$_3$ group-modified silica sol from Comparative Example (1) into 46.5 g of ethanol, and heating under reflux overnight, 50.0 g of ethanol solution comprising the antifog additive of the present invention was obtained.

Example 7

By adding 1.0 g of ethanol solution from (2) of Example 3 to 49.0 g of ethanol solution from (2) of Example 6, and heating under reflux overnight, 50.0 g of ethanol solution comprising the antifog additive of the present invention was obtained.

Example 8

(1) By stirring 4.81 g (50.0 mmol) of 3,5-dimethylpyrazol and 12.35 g (50.0 mmol) of 3-isocyanatepropyltriethoxysilane at room temperature for 3 days, 16.8 g of blocked isocyanate compound in which isocyanate group of 3-isocyanatepropyltriethoxysilane is blocked by 3,5-dimethylpyrazol was obtained. Through 1H-NMR detection, it was confirmed that the absorption of proton (3.27-3.32 ppm) of carbon which is bonded to isocyanate group of 3-(triethoxysilyl)propylisocyanate-raw material-disappeared and newly the absorption of proton (3.32-3.39 ppm) of carbon which is bonded to urea group of the object appeared.

(2) By adding 1.0 g of blocked isocyanate compound from (1) into 49.0 g of ethanol solution comprising $LiOSO_2$—$CH_2CH_2CH_2Si$(—O—)$_3$ group-modified isopropanol silica sol from Comparative Example (1), and stirring them at room temperature for 3 days, 50.0 g of ethanol solution comprising $LiOSO_2$—$CH_2CH_2CH_2Si$(—O—)$_3$ group and blocked isocyanate group-modified silica sol (2.83 mmol of lithium sulfonate and 1.61 mmol of blocked isocyanate group are bonded based on 1 g of silica sol) was obtained.

(3) By adding 1.0 g of 3-(trimethoxysilyl)propane-1-thiol (CHISSO CORPORATION) to 49.0 g of ethanol solution comprising $LiOSO_2$—$CH_2CH_2CH_2Si$(—O—)$_3$ group-modified isopropanol silica sol from Comparative Example (1), and stirring them at room temperature for 3 days, 50.0 g of ethanol solution comprising $LiOSO_2$—$CH_2CH_2CH_2Si$(—O—)$_3$ group and thiol group-modified silica sol (2.83 mmol of lithium sulfonate and 2.78 mmol of thiol group are bonded based on 1 g of silica sol) was obtained.

(4) After dissolving 3.0 g (15.3 mmol) of 3-(trimethoxysilyl)propane-1-thiol (CHISSO CORPORATION) and 2.4 g of surface-active silane coupling agent from (1) of Example 3 into 80 g of ethanol, 18.0 g of organosilica sol (30% isopropanol solution, IPA-ST from NISSAN CHEMICAL INDUSTRIES, LTD.) and 19.5 g of water were added to them, and heating under reflux was conducted for 24 hours. After cooling the mixture, 10.5 parts by weight (463 mmol) of hydrogen peroxide water (SANTOKU CHEMICAL INDUSTRIES CO., LTD., 30% aqueous solution) was added to it, and heating under reflux was conducted for 24 hours. After termination of reaction, the mixture was cooled to room temperature, and 0.97 g (27.9 mmol) of lithium hydroxide monohydrate dissolved in 12 g of water was added to it for neutralization. In addition, by adding water to the mixture to make its weight 150 g, 150.0 g of ethanol solution comprising ethylene oxide adduct group of dodecyl alcohol and $LiOSO_2$—$CH_2CH_2CH_2Si$ group-modified silica sol (2.83 mmol of lithium sulfonate and about 1.55 mmol of ethylene oxide adduct group of dodecyl alcohol are bonded based on 1 g of silica sol) was obtained.

(5) By dissolving 2.5 g of ethanol solution from (2), 2.5 g of ethanol solution from (3) and 5.0 g of ethanol solution from (4) into 40.0 g of ethanol solution and heating under reflux overnight, 50.0 g of ethanol solution comprising the antifog additive of the present invention was obtained.

Evaluation of Antifog Effect

The surfaces of the below substrates were modified by the antifog additives from Comparative Example 1 and Examples 1 to 8, the substrates were placed on the top of a hot tub of 70° C. and the antifog effect (checking occurrence of fogging when exposed to steam) was evaluated. The result is shown in Table 1.

Comparative Example 1 and Examples 1-7: Slide Glass, Example 8: Polycarbonate (1) A slide glass (76 mm, 26 mm, 1.2 mm; which was immersed into a saturated solution of 2-propanol of sodium hydroxide for 24 hours, and washed and dried [60° C., 2 hours]) was immersed into treating solution (the antifog additive for surface). After taking out the slide glass, liquid was removed and heat treatment was conducted at 120° C. for 1 hour to obtain a surface-antifogging treated slide glass.

(2) A polycarbonate plate (76 mm, 26 mm, 1.0 mm; washed by ethanol) was immersed into treating solution (the antifog additive for surface). After taking out the polycarbonate plate, liquid was removed and heat treatment was conducted at 130° C. for 1 hour to obtain a surface-antifogging treated polycarbonate plate.

TABLE 1

|  | Antifog effect |
| --- | --- |
| Comparative Example 1 | X |
| Example 1 | ○ |
| Example 2 | ○ |
| Example 3 | ○ |
| Example 4 | ○ |
| Example 5 | ○ |
| Example 6 | ○ |
| Example 7 | ○ |
| Example 8 | ○ |

X: The antifog effect does not work (fogging)
○: The antifog effect works (no fogging)

The present inventors tested various functional groups containing S-modified metal oxide sols disclosed in the Examples of Patent Document 1 besides Comparative Example 1, and could not discern the antifog effect.

As shown in the result, it is obvious that the modified metal oxide sol of the present invention shows the antifog effect.

INDUSTRIAL APPLICABILITY

Since the antifog additive comprising the modified metal oxide sol has a good antifog effect for glass or plastic, etc., it is suitable as an antifog additive for glass, lens of eyeglasses, optical lens, mirror, etc. Moreover, since the antifog additive is coatable and prepared at low cost, it is suitable as a hydrophilizing agent, an antistatic agent, a hydrophilic coating composition, antimicrobial agent, ion (proton) conductor as well as an antifog additive.

What is claimed is:
1. A modified metal oxide sol comprising a mixture and/or condensation product of
   a hydrolysate of a surface-active silane coupling agent, a modified metal oxide sol that is modified by a hydrolysate of the surface-active silane coupling agent or a mixture and/or condensation product of a hydrolysate of the surface-active silane coupling agent and a modified metal oxide sol that is modified by a hydrolysate of surface-active silane coupling agent; and a modified metal oxide sol that is modified by a functional group containing sulfur (S) (hereinafter referred as "a functional group containing S-modified metal oxide sol") as main components, wherein the surface-active silane coupling agent is a reaction product of a compound represented by the following Formula (1) and a silane coupling agent having a functional group which can react with active hydrogen of Formula (1), and the functional group containing S-modified metal oxide sol is a modified metal oxide sol in which 0.5 mmol or more of metal oxide sol based on 1 g of metal oxide sol is modified by a functional group represented by the following Formula (2):

$$R^1—X—(CH_2CH_2O)_n—Y \quad (1)$$

wherein $R^1$ is $C_1$ to $C_{20}$ alkyl group (the alkyl group may comprise a benzene ring and double bond);

X is —O—, —COO— or —CONH—;

n is a natural number of 1 to 30; and

Y is hydrogen or —CH$_2$COOH;

$$MOS(=O)_2—R^2—Si(CH_3)_n(—O—)_{3-n} \quad (2)$$

wherein M is hydrogen ion, $C_1$ to $C_4$ alkyl group, a metal ion or an ammonium group (NR$^3_4$);

$R^2$ is $C_1$ to $C_{10}$ alkylene group (the alkylene chain may comprise urethane linkage or urea linkage);

$R^3$ is the same or different $C_1$ to $C_5$ alkyl group or hydrogen; and n is 0 or 1.

2. The modified metal oxide sol according to claim 1, further comprising at least one of the silicon-based compounds represented by the following Formula (3):

$$X—(R^4)_m—Si(CH_3)_n(—Y)_{3-n} \quad (3)$$

wherein X is selected from the group consisting of $C_1$ to $C_{20}$ linear or branched alkyl group, vinyl group, thiol group, amino group, chlorine atom, acryl group, methacryl group, styryl group, phenyl group, glycydoxy group, 3,4-epoxycyclohexyl group and blocked isocyanate group;

$R^4$ is $C_1$ to $C_5$ alkylene group;

m is 0 or 1;

Y is the same or different $C_1$ to $C_4$ alkoxy group or hydroxyl group; and n is 0 or 1.

3. The modified metal oxide sol according to claim 2, wherein the metal oxide sol is organosilica sol.

4. An antifog additive comprising the modified metal oxide sols according to claim 2.

5. An antifog coating composition comprising the modified metal oxide sols according to claim 2.

6. The modified metal oxide sol according to claim 1, wherein the metal oxide sol is organosilica sol.

7. An antifog additive comprising the modified metal oxide sols according to claim 6.

8. An antifog coating composition comprising the modified metal oxide sols according to claim 6.

9. An antifog additive comprising the modified metal oxide sols according to claim 1.

10. An antifog coating composition comprising the modified metal oxide sols according to claim 9.

11. An antifog coating composition comprising the modified metal oxide sols according to claim 1.

12. A structure which is obtained by coating and curing the antifog coating composition according to claim 11.

* * * * *